US009435749B2

(12) United States Patent
Winchip et al.

(10) Patent No.: US 9,435,749 B2
(45) Date of Patent: Sep. 6, 2016

(54) SYSTEM AND METHOD FOR INSPECTION OF ROLL SURFACE

(71) Applicants: Wade A. Winchip, Bettendorf, IA (US); David Anderson, Townsend, TN (US); Kelly Pepper, Evansville, IN (US); Neville Whittle, Irwin, PA (US)

(72) Inventors: Wade A. Winchip, Bettendorf, IA (US); David Anderson, Townsend, TN (US); Kelly Pepper, Evansville, IN (US); Neville Whittle, Irwin, PA (US)

(73) Assignee: Alcoa Inc., Pittsburgh, PA (US)

( * ) Notice: Subject to any disclaimer, the term of this patent is extended or adjusted under 35 U.S.C. 154(b) by 267 days.

(21) Appl. No.: 14/208,990

(22) Filed: Mar. 13, 2014

(65) Prior Publication Data

US 2014/0267887 A1  Sep. 18, 2014

Related U.S. Application Data

(60) Provisional application No. 61/780,270, filed on Mar. 13, 2013.

(51) Int. Cl.
*H04N 5/235* (2006.01)
*G01N 21/952* (2006.01)

(52) U.S. Cl.
CPC .................. *G01N 21/952* (2013.01)

(58) Field of Classification Search
None
See application file for complete search history.

(56) References Cited

U.S. PATENT DOCUMENTS

| 6,674,553 | B1* | 1/2004 | Ito | G06F 3/002 353/25 |
|---|---|---|---|---|
| 2006/0203229 | A1* | 9/2006 | Gotoh | G01N 21/952 356/237.1 |
| 2007/0177137 | A1* | 8/2007 | Kamada | G01B 11/2527 356/237.2 |
| 2011/0279828 | A1* | 11/2011 | Matsumoto | F22B 37/005 356/630 |
| 2014/0211200 | A1* | 7/2014 | Kim | G01M 11/31 356/73.1 |

* cited by examiner

*Primary Examiner* — Kate Luo
(74) *Attorney, Agent, or Firm* — Greenberg Traurig, LLP

(57) ABSTRACT

A system and method that includes, in an embodiment, a prism, a camera, a light source, and a plate. The system, in an embodiment, is configured for scanning a roll and generating an image of the roll surface. The prism, in an embodiment, is positioned below the camera and above the plate. In an embodiment, the plate is positioned below the prism and above the roll surface. In an embodiment, the light source is positioned above the prism. In an embodiment, the light source and the prism are positioned to provide light to the roll surface at an angle of at least 75 degrees measured from a line normal to the roll surface. In an embodiment, the prism is configured to refract light from the light source, the camera is a line scan camera that includes a row of pixel sensors, and the light source includes light emitting diodes.

7 Claims, 12 Drawing Sheets

SYSTEM AND METHOD FOR INSPECTION OF ROLL SURFACE

RELATED APPLICATIONS

This application claims the benefit of U.S. Provisional Application No. 61/780,270, entitled "SYSTEM AND METHOD FOR WET INSPECTION OF ROLL SURFACE," filed Mar. 13, 2013, which is hereby incorporated by reference herein in its entirety for all purposes.

TECHNICAL FIELD

The system and method relate to inspection of a roll used for hot or cold rolling metal.

BACKGROUND

Methods for inspecting roll surfaces are known.

SUMMARY OF INVENTION

In some embodiments, the system includes: (i) a prism, (ii) a camera, (iii) a light source, and (iv) a plate. In some embodiments, the system is configured for scanning a roll and generating an image of a surface of the roll. In some embodiments, the prism is positioned below the camera and above the plate. In some embodiments, the plate is positioned below the prism and on or above the surface of the roll.

In some embodiments, the light source is positioned above the prism. In some embodiments, the light source and the prism are positioned to provide light to the surface of the roll at an angle of at least 75 degrees as measured from a line normal to the surface of the roll. In some embodiments, the prism is configured to refract light from the light source. In some embodiments, the camera is a line scan camera that includes at least one row of pixel sensors. In some embodiments, the light source includes one or more light emitting diodes.

In some embodiments, the plate is positioned between 0.005 inches and 0.05 inches from the roll. In some embodiments, the plate is positioned between 0.005 and 0.020 inches from the roll. In some embodiments, the plate is positioned 0.005 inches from the roll.

In some embodiments, the coolant is positioned between the plate and the roll. In some embodiments, the plate comprises a polymeric material. In some embodiments, the light source and the prism are positioned to provide light at an angle of 78 degrees as measured from the line normal to the surface of the roll.

In some embodiments, the method includes lighting a surface of a roll using a light source and a prism. In some embodiments, the light source and the prism are positioned to provide light to the surface of the roll at an angle of at least 75 degrees as measured from a line normal to the surface of the roll. In some embodiments, the method further includes receiving, by at least one specifically programmed computer system, a plurality of lines from a line scan camera while the roll is rotating. In some embodiments, each line corresponds to a section of the roll.

In some embodiments, the method includes creating, by the at least one specifically programmed computer system, a plurality of frames based, at least in part, on the plurality of lines. In some embodiments, the method includes generating, by the at least one specifically programmed computer system, the two-dimensional image of the surface of the roll based, at least in part, on the plurality of frames.

In some embodiments, the plurality of lines is received at a speed of 1000 to 5000 lines per second. In some embodiments, each of the plurality of frames is formed of at least 1000 lines. In some embodiments, the surface of the roll is at least partially covered by a fluid during the receiving step. In some embodiments, the line scan camera moves in a transverse direction relative to the roll during the receiving step.

In some embodiments, a first speed of the rotating roll is greater than a second speed of the moving line scan camera. In some embodiments, the first resolution of the image in the transverse direction is less than a second resolution of the image in a circumferential direction.

In some embodiments, the method includes lighting a surface of a roll using a light source and a prism. In some embodiments, the light source and the prism are positioned to provide light to the surface of the roll at an angle of at least 75 degrees as measured from a line normal to the surface of the roll. In some embodiments, the method includes receiving, by at least one specifically programmed computer system, a plurality of lines from a line scan camera while the roll is rotating. In some embodiments, each line corresponds to a section of the roll.

In some embodiments, the method includes creating, by the at least one specifically programmed computer system, a plurality of frames based, at least in part, on the plurality of lines. In some embodiments, the method includes generating, by the at least one specifically programmed computer system, the two-dimensional image of the surface of the roll based, at least in part, on the plurality of frames. In some embodiments, the method includes evaluating, by the at least one specifically programmed computer system, defects on the roll based, at least in part, on the two-dimensional image of the surface of the roll. In some embodiments, the method includes grinding the roll based, at least in part, on the evaluation of the defects on the roll.

In some embodiments, the evaluating step and the generating step are conducted concomitantly. In some embodiments, the evaluating step and the grinding step are conducted concomitantly. In some embodiments, the surface of the roll is at least partially covered by a fluid during the receiving step. In some embodiments, the line scan camera moves in a transverse direction relative to the roll during the receiving step.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

Figure 1:
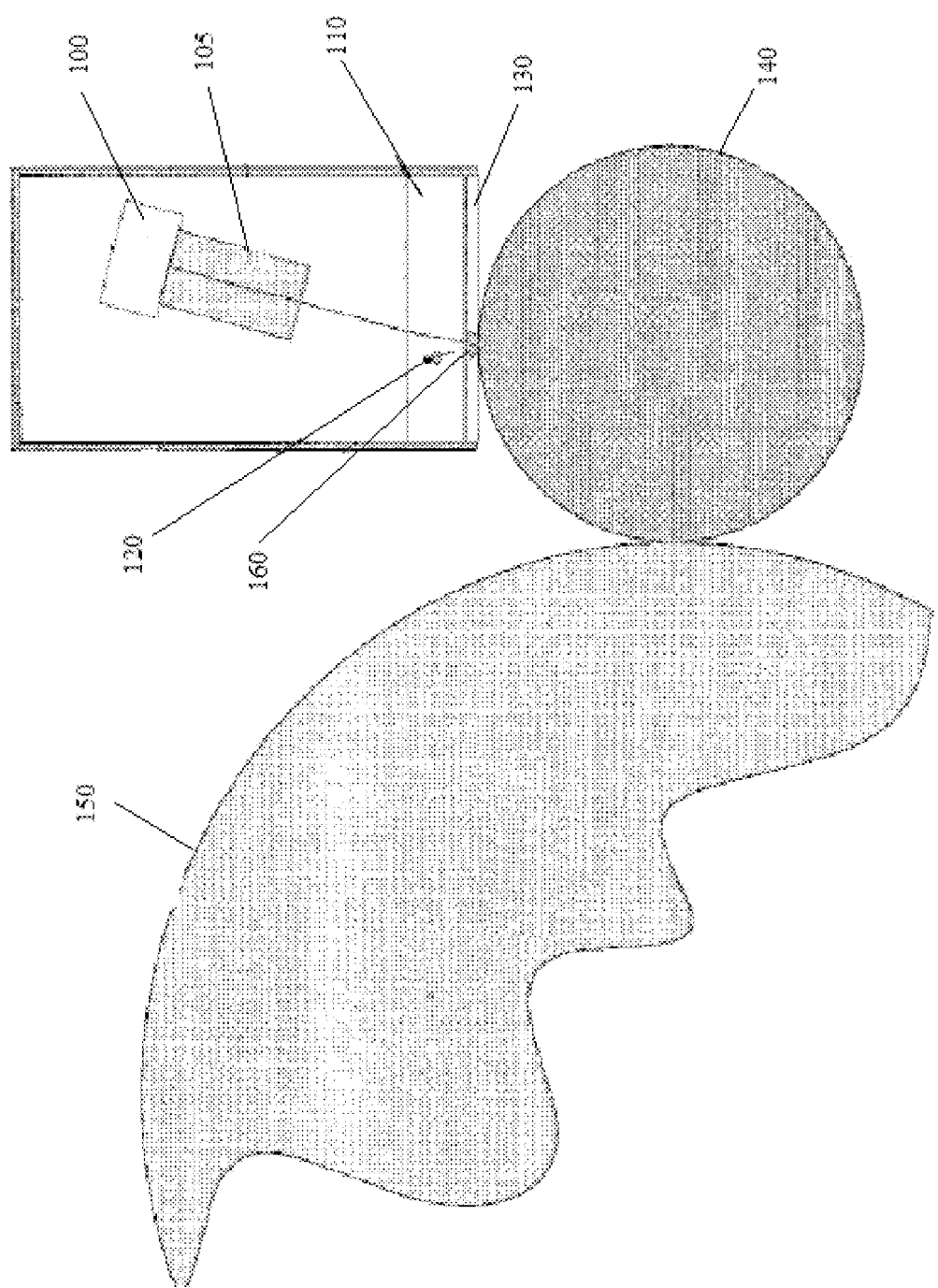
FIG. 1 illustrates features of some embodiments of the present invention.

The figures constitute a part of this specification and include illustrative embodiments of the present invention and illustrate various objects and features thereof. Further, the figures are not necessarily to scale, some to features may be exaggerated show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, the system includes: (i) a prism, (ii) a camera, (iii) a light source, and (iv) a plate. In some embodiments, the system is configured for scanning a roll and generating an image of a surface of the roll. In some embodiments, the prism is positioned below the camera and above the plate. In some embodiments, the plate is positioned below the prism and on or above the surface of the roll.

In some embodiments, the light source is positioned above the prism. In some embodiments, the light source and the prism are positioned to provide light to the surface of the roll at an angle of at least 75 degrees as measured from a line normal to the surface of the roll. In some embodiments, the prism is configured to refract light from the light source. In some embodiments, the camera is a line scan camera that includes at least one row of pixel sensors. In some embodiments, the light source includes one or more light emitting diodes.

In some embodiments, the plate is positioned between 0.005 inches and 0.05 inches from the roll. In some embodiments, the plate is positioned between 0.005 and 0.020 inches from the roll. In some embodiments, the plate is positioned 0.005 inches from the roll.

In some embodiments, the coolant is positioned between the plate and the roll. In some embodiments, the plate comprises a polymeric material. In some embodiments, the light source and the prism are positioned to provide light at an angle of 78 degrees as measured from the line normal to the surface of the roll.

In some embodiments, the method includes lighting a surface of a roll using a light source and a prism. In some embodiments, the light source and the prism are positioned to provide light to the surface of the roll at an angle of at least 75 degrees as measured from a line normal to the surface of the roll. In some embodiments, the method further includes receiving, by at least one specifically programmed computer system, a plurality of lines from a line scan camera while the roll is rotating. In some embodiments, each line corresponds to a section of the roll.

In some embodiments, the method includes creating, by the at least one specifically programmed computer system, a plurality of frames based, at least in part, on the plurality of lines. In some embodiments, the method includes generating, by the at least one specifically programmed computer system, the two-dimensional image of the surface of the roll based, at least in part, on the plurality of frames.

In some embodiments, the plurality of lines is received at a speed of 1000 to 5000 lines per second. In some embodiments, each of the plurality of frames is formed of at least 1000 lines. In some embodiments, the surface of the roll is at least partially covered by a fluid during the receiving step. In some embodiments, the line scan camera moves in a transverse direction relative to the roll during the receiving step.

In some embodiments, a first speed of the rotating roll is greater than a second speed of the moving line scan camera.

In some embodiments, the first resolution of the image in the transverse direction is less than a second resolution of the image in a circumferential direction.

In some embodiments, the method includes lighting a surface of a roll using a light source and a prism. In some embodiments, the light source and the prism are positioned to provide light to the surface of the roll at an angle of at least 75 degrees as measured from a line normal to the surface of the roll. In some embodiments, the method includes receiving, by at least one specifically programmed computer system, a plurality of lines from a line scan camera while the roll is rotating. In some embodiments, each line corresponds to a section of the roll.

In some embodiments, the method includes creating, by the at least one specifically programmed computer system, a plurality of frames based, at least in part, on the plurality of lines. In some embodiments, the method includes generating, by the at least one specifically programmed computer system, the two-dimensional image of the surface of the roll based, at least in part, on the plurality of frames. In some embodiments, the method includes evaluating, by the at least one specifically programmed computer system, defects on the roll based, at least in part, on the two-dimensional image of the surface of the roll. In some embodiments, the method includes grinding the roll based, at least in part, on the evaluation of the defects on the roll.

In some embodiments, the evaluating step and the generating step are conducted concomitantly. In some embodiments, the evaluating step and the grinding step are conducted concomitantly. In some embodiments, the surface of the roll is at least partially covered by a fluid during the receiving step. In some embodiments, the line scan camera moves in a transverse direction relative to the roll during the receiving step.

Traditional mills may include a metal forming process called rolling. Rolling includes passing metal including, but not limited to, aluminum, through a pair of rolls. Depending on the temperature, rolling may be classified as "hot" rolling or "cold" rolling.

The rolling process typically results in defects in the surface of each roll. For example, metal may adhere to the roll during the rolling process. These defects in the surface of each roll affect the quality of the rolled product and thus require removal.

Typically, the defects on the surface of the roll are removed using a grinding process or equivalent. The grinding process may include contacting the surface of the roll with a grinding wheel to remove the defects. To prevent heat buildup and wash away grinding debris, the grinding process also typically includes a coolant directed towards the wheel and roll contact. This coolant includes, but is not limited to, a water-based coolant, prior to or concurrent with grinding.

In some embodiments, the present invention includes a method and system for wet inspection of the roll surface during grinding. In some embodiments, the system includes a roll, a prism, a camera, a light source, and a plate; wherein the prism is positioned between the camera and the roll and configured to refract light from the light source; wherein the camera includes one row of pixel sensors; wherein the light source includes one or more light emitting diodes; wherein the one or more light emitting diodes are configured to provide light at an angle greater than or equal to 75 degrees as measured from a line normal to a surface of the roll; wherein the plate is positioned between the camera and the surface of the roll and located greater than 0.005 inches and less than 0.05 inches from the roll.

In some embodiments, the system includes a camera 100 (200, 300, 400, 500, 600) with lens 105 (405, 605), a prism 110 (310, 510, 610), a light source 120 (220, 320, 420, 620), a plate 130 (230, 330, 430, 530) and a roll 140 (240, 440, 540, 640) as shown in FIGS. 1-6. In some embodiments, the plate 130 includes one or more apertures 160 (360).

In some embodiments, FIG. 1 also shows a non-limiting example of a grinding wheel 150. In some embodiments, the grinding wheel is 36" diameter. In some embodiments, the grinding wheel is 24" diameter. In some embodiments, the grinding wheel is 48" diameter. In some embodiments, the grinding wheel is greater than 48" diameter. In some embodiments, the grinding wheel is less than 24" diameter. In some embodiments, the grinding wheel is 56" diameter. In some embodiments, the grinding wheel is 60" diameter.

Figure 2:
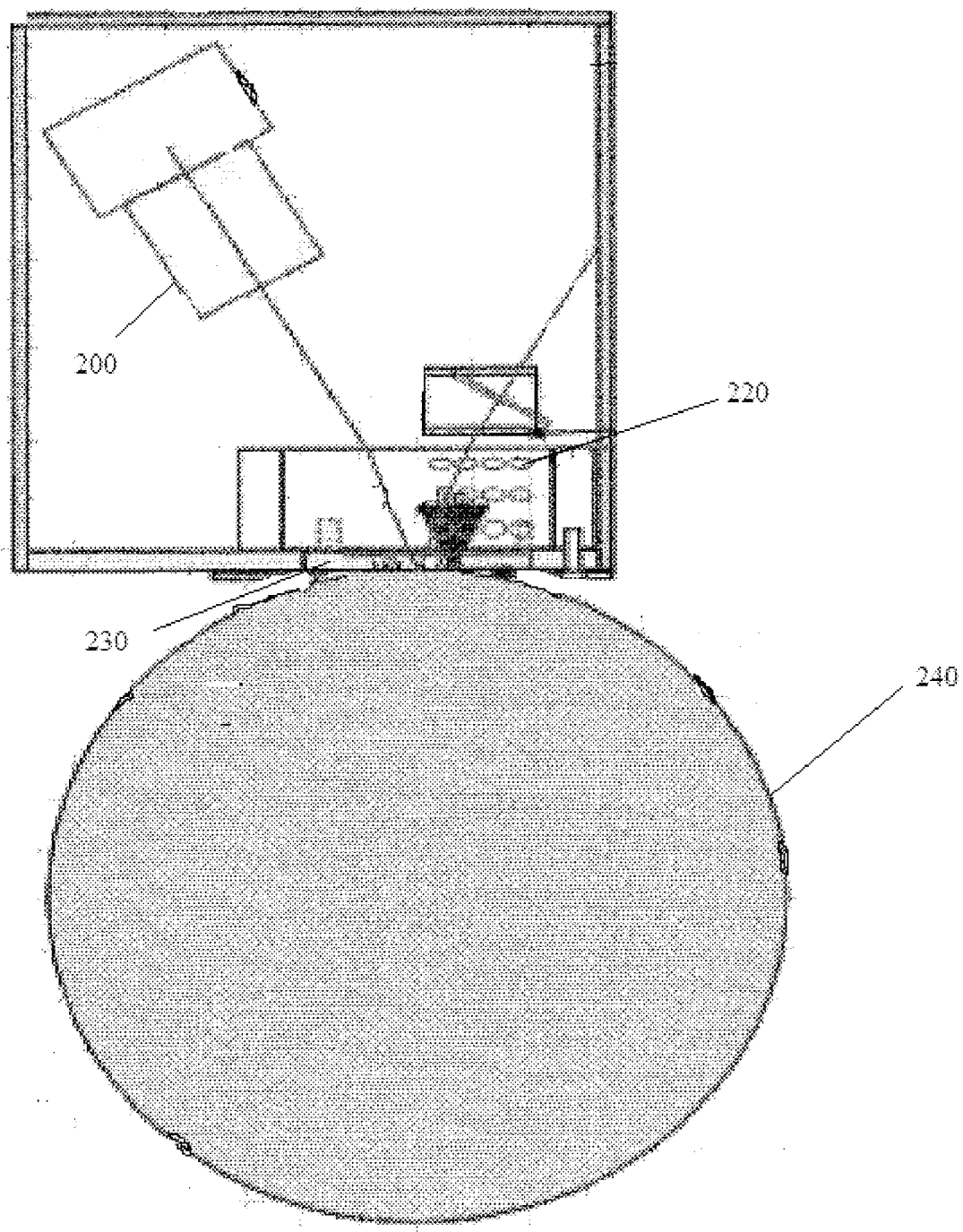
FIG. 2 illustrates features of some embodiments of the present invention.
Figure 3:
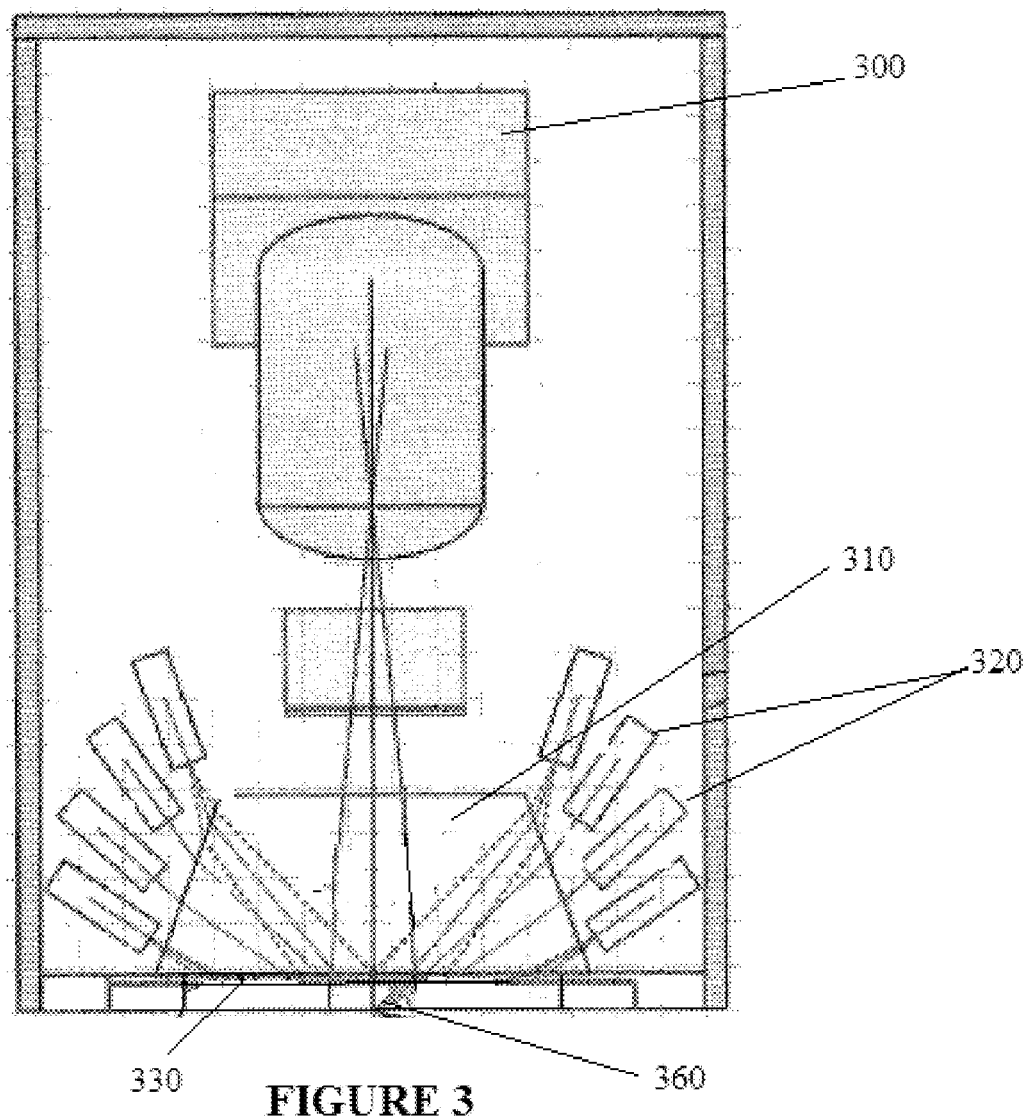
FIG. 3 illustrates features of some embodiments of the present invention.
Figure 4:
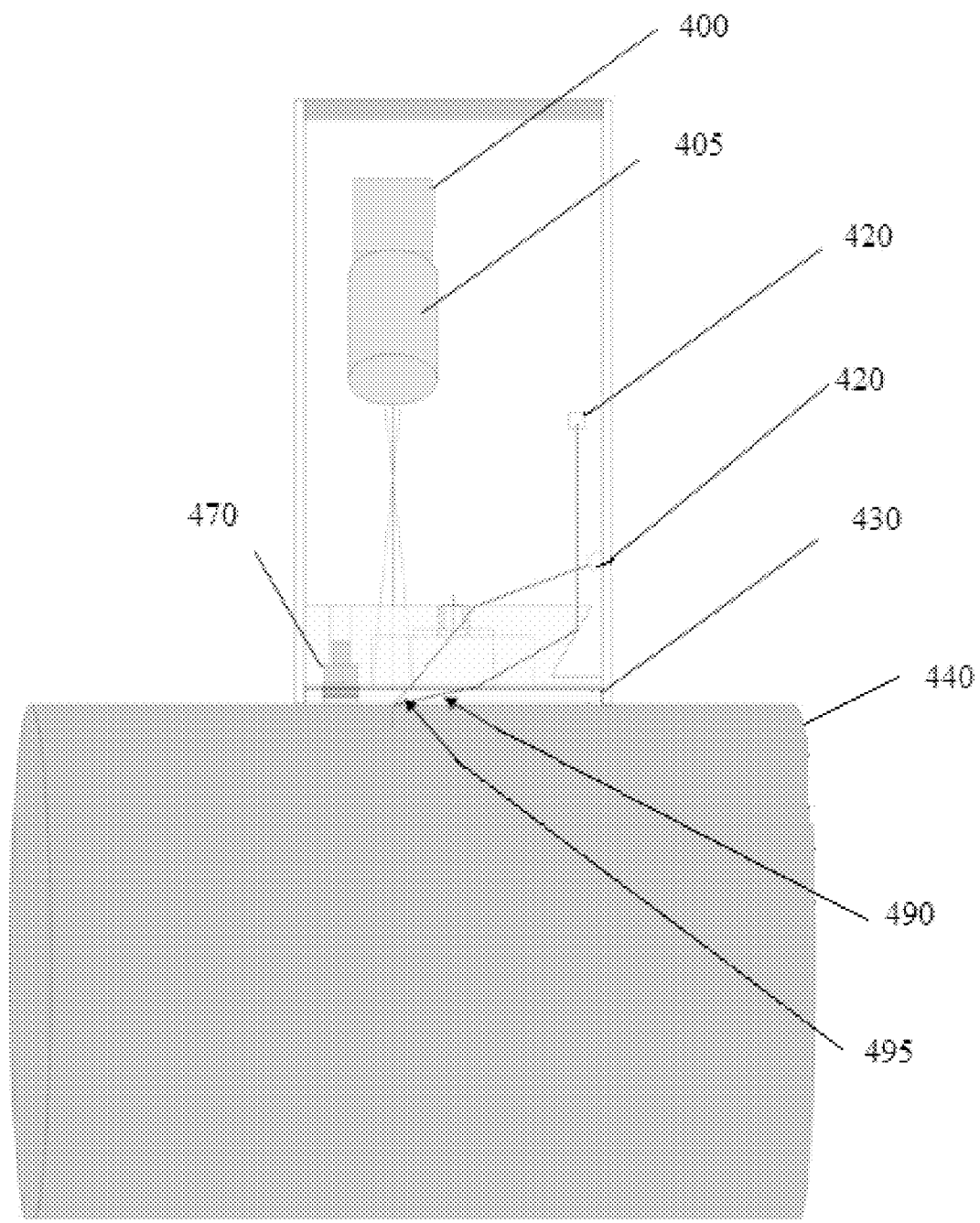
FIG. 4 illustrates features of some embodiments of the present invention.
Figure 5:
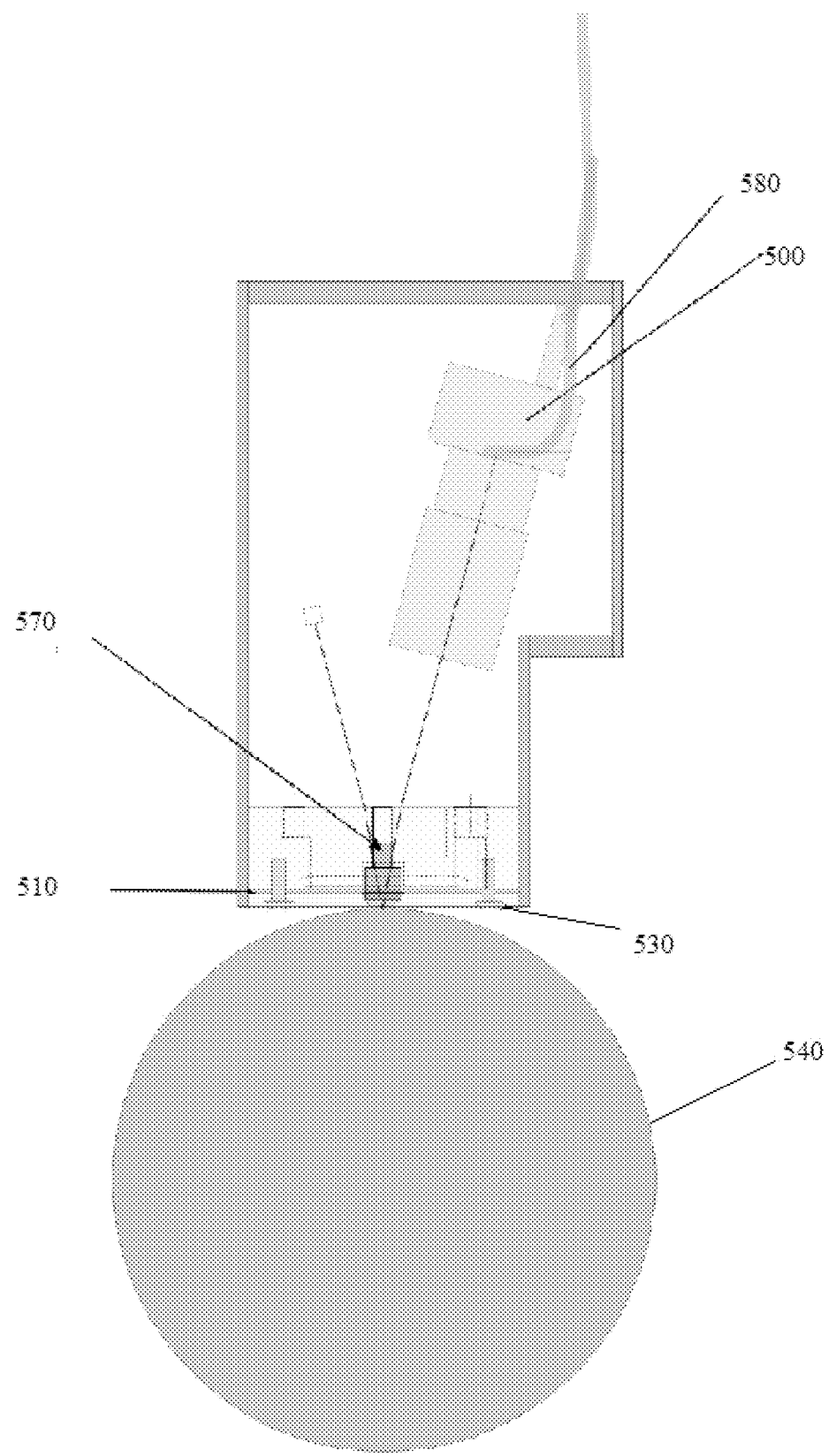
FIG. 5 illustrates features of some embodiments of the present invention.

FIGS. 2-6 show multiple embodiments of the system of the present invention. FIG. 2 shows an embodiment that includes a light source 220 comprising multiple light emitting diodes. FIG. 4 also shows an embodiment where the light contacts the surface of the roll 440 at an angle 490 (690) of 78 degrees from a line normal to the roll. FIG. 4 also shows an embodiment where the light contacts the surface of the roll at an angle 495 (695) of 45 degrees from a line normal to the roll. FIG. 4 also illustrate additional components of an embodiment of a system of the present invention such as a gap control sensor 470 (570). FIG. 5 illustrates a coolant delivery device such as a hose 580 of an embodiment of the present invention.

Figure 6:
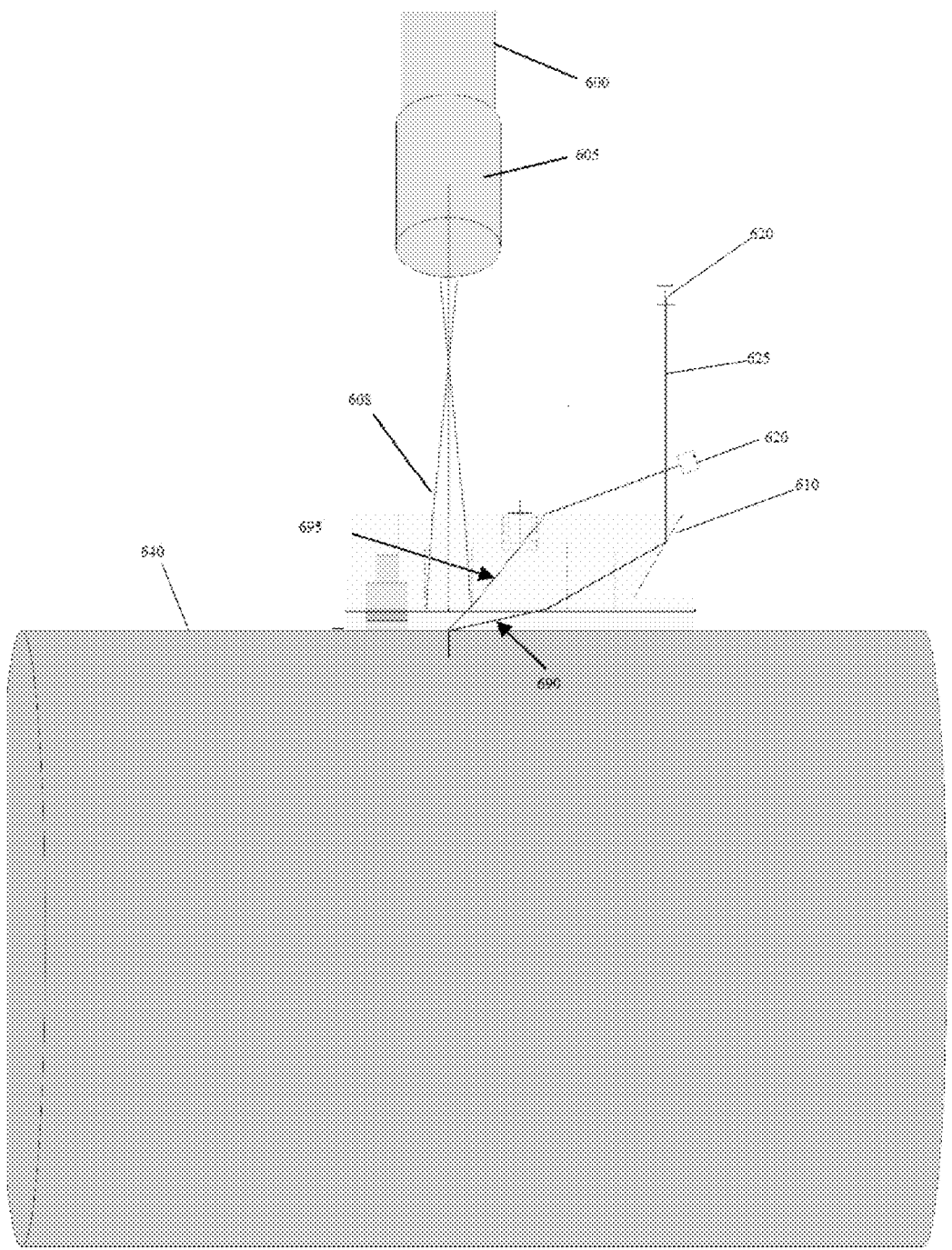
FIG. 6 illustrates features of some embodiments of the present invention.

FIG. 6 shows the light path 625 of light emitted from a light source 620 in an embodiment of the present invention. FIG. 6 also shows a field of view 608 of the camera of an embodiment of the present invention.

In some embodiments, the camera is a line scan camera. In some embodiments, the camera is a digital camera that includes a sensor with a single line of light sensing pixels. In some embodiments, the camera provides different pixel resolution in the transverse and circumferential directions relative to the roll and thus reduces the amount of image data requiring subsequent processing. In some embodiments, the line of pixels associated with the line scan camera is aligned along a long axis of the roll. In some embodiments, the camera uses the line of pixels to continuously scan the roll and thus generate an image of the roll surface. In some embodiments, the line scan camera is a Dalsa Technology Piranha2 Model P2-2x-xxx40.

In some embodiments, the prism refracts the light from the light source to correct the distortion of light associated with i) the wetted roll, ii) coolant positioned between the roll and/or iii) the plate positioned between the prism and the coolant. In some embodiments, the angles of the facets of the prism are configured to correct the refraction of light from air, the plate material, and/or coolant. In some embodiments, the prism is positioned such that the light from the light source travels through one or more flat surfaces or faces of the prism. In some embodiments, the prism is positioned such that the light from the light source travels through one or more edges of the prism. In some embodiments, each edge of the prism is formed when the flat surfaces or faces of the prism intersect. In some embodiments, the prism is positioned a sufficient distance from the roll surface so as to result in protection of the prism from debris from the grinding process.

In some embodiments, the distance between the prism and roll surface is 0.03 inches to 0.7 inches. In some embodiments, the distance between the prism and roll surface is 0.03 inches to 0.5 inches. In some embodiments, the distance between the prism and roll surface is 0.03 inches to 0.3 inches. In some embodiments, the distance between the prism and roll surface is 0.03 inches to 0.1 inches. In some embodiments, the distance between the prism and roll surface is 0.1 inches to 0.7 inches. In some embodiments, the distance between the prism and roll surface is 0.3 inches to 0.7 inches. In some embodiments, the distance between the prism and roll surface is 0.5 inches to 0.7 inches.

Figure 7B:
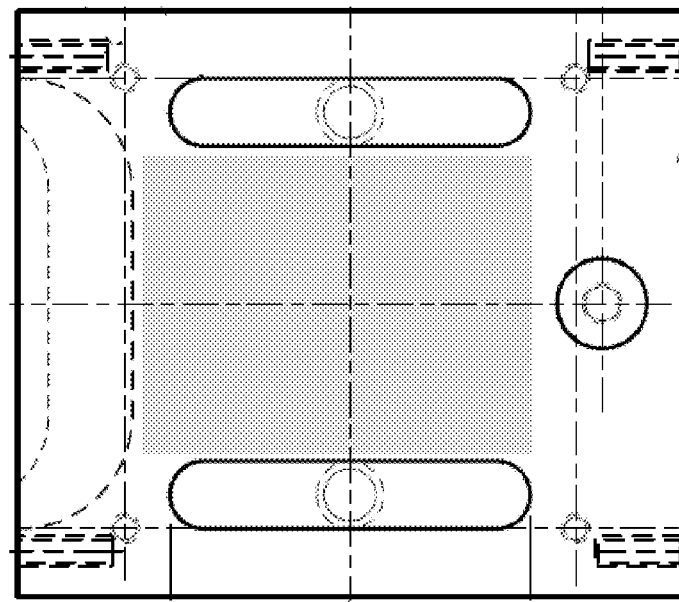
FIG. 7A-7D illustrate features of some embodiments of the present invention.
Figure 7A:
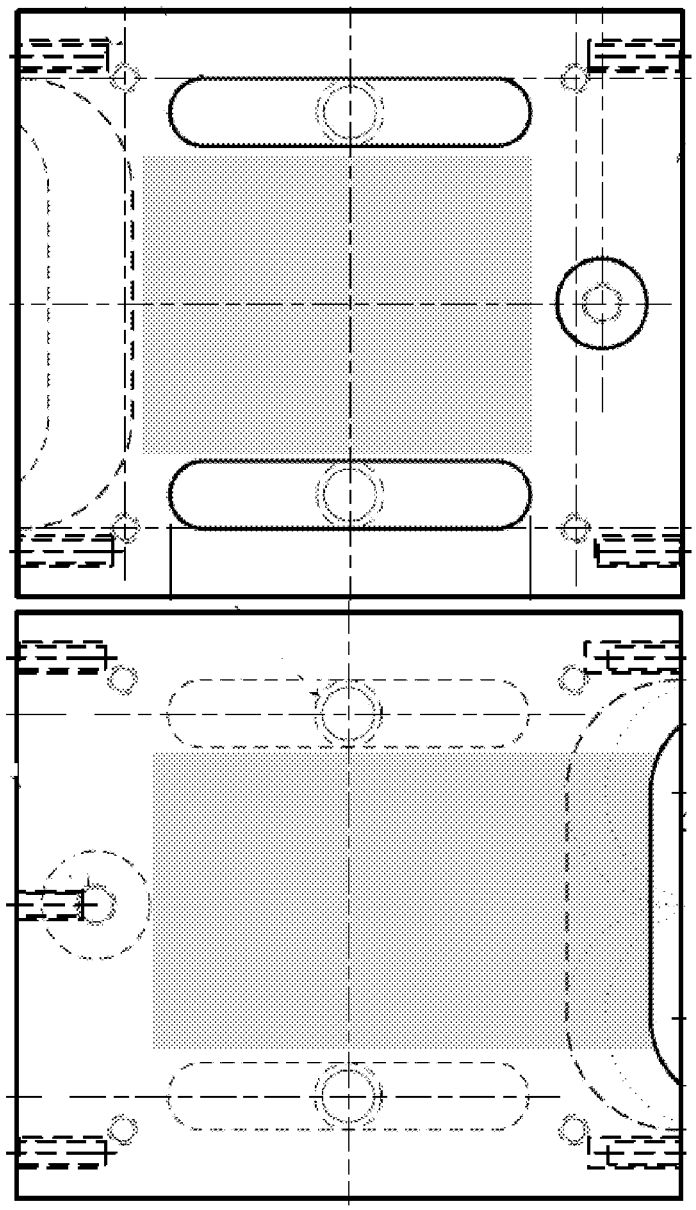
Figure 7D:
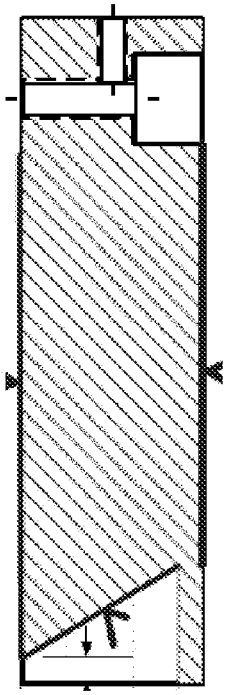
Figure 7C:
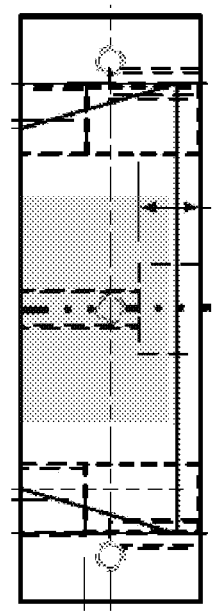

In some embodiments, the prism is formed of a material capable of refracting light. In some embodiments, the prism is formed of acrylic or other polymeric material. In some embodiments, the prism is formed of glass. In some embodiments, the prism is translucent. In some embodiments, the prism is polished so as to be optically clear and substantially free of any scratches or visible defects. FIGS. 7A and 7B are top and bottom views, respectively, of a non-limiting example of the prism of the present invention. FIG. 7C is a front view of a non-limiting example of the prism of the present invention. FIG. 7D is a cross-sectional view of a non-limiting example of the prism of the present invention.

In some embodiments, the light source includes one or more lights for illumination of the mill roll. In some embodiment the lights may include, but are not limited to, incandescent lamps, lasers, light emitting diodes, and/or other light source sufficient for illuminating the mill roll. In some embodiments, the one or more lights is positioned at an angle of greater than 45 degrees and less than 90 degrees as measured from a line normal to the rolling surface. In some embodiments, the one or more lights is positioned at an angle of greater than 60 degrees and less than 90 degrees from normal as measured from a line normal to the roll surface. In some embodiments, the one or more lights is positioned at an angle of greater than 70 degrees and less than 90 degrees from normal as measured from a line normal to the rolling surface. In some embodiments, the one or more lights is positioned at an angle of greater than or equal to 75 degrees and less than 90 degrees from normal as measured from a line normal to the rolling surface. In some embodiments, the one or more lights is positioned at an angle of 78 degrees from normal as measured from a line normal to the rolling surface. In some embodiments, the one or more lights are positioned as shown in FIGS. 1-6.

In some embodiments, the plate is positioned between the prism and the surface of the roll. In some embodiments, the plate includes one or more apertures 160 (860) to allow the light source to illuminate the roll surface and provide the camera a view the surface of the roll. In some embodiments, the angle of the side wall of the aperture relative to a line normal to plate is 30 degrees. In some embodiments, the angle of the side wall of the aperture relative to a line normal to plate is 40 degrees. In some embodiments, the angle of the side wall of the aperture relative to a line normal to plate is 15 degrees. In some embodiments, the angle of the side wall of the aperture relative to a line normal to plate is 45 degrees. In some embodiments, the angle of the side wall of the aperture relative to a line normal to plate is 60 degrees.

In some embodiments, the one or more apertures is at least partially filled with coolant. In some embodiments, the one or more apertures is filled with coolant. In some embodiments, the one or more apertures is filled with fluid from a source other than the coolant. In some embodiments, the fluid used to at least partially fill the one or more apertures is different than the coolant used to remove heat generated from grinding. In some embodiments, the fluid used to at least partially fill the one or more apertures and the coolant used to remove the heat generated from grinding are supplied via separate feed lines, spouts, nozzle, and/or distribution valves.

In some embodiments, the coolant may be diluted using a water supply before use as fluid to at least partially fill the at least one apertures. In some embodiments, the coolant and/or the fluid used to at least partially fill the at least one apertures may include water and at least one surface configured to reduce or eliminate rust buildup on the roll surface.

In some embodiments, the plate provides flow control of the coolant by create a seal with the roll surface. In some embodiments, the coolant flows through the aperture of the plate and then exits through one or more holes in the plate. In some embodiments, the plate does not contact the rolling surface.

Figure 8A:
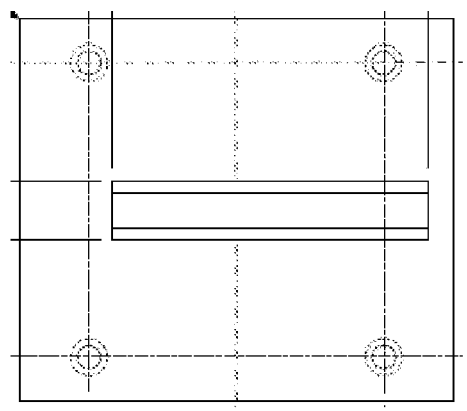
FIG. 8A-8C illustrate features of some embodiments of the present invention.
Figure 8B:
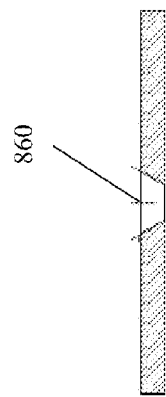
Figure 8C:
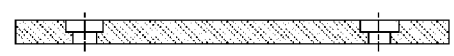

In some embodiments, the plate is formed of plastic. In some embodiments, the plate is formed of glass. In some embodiments, the plate is formed of a polymeric material. In some embodiments, the plate is either transparent or translucent. FIG. 8A shows a top view of a non-limiting example of the plate of the present invention. FIGS. 8B and 8C show cross-sectional views of a non-limiting example of the plate of the present invention.

In some embodiments, the distance between the plate and the roll is greater than 0 and less than 1 inch. In some embodiments, the distance between the plate and the roll is greater than 0 and less than 0.1 inch. In some embodiments, the distance between the plate and the roll is greater than 0 and less than 0.05 inch. In some embodiments, the distance between the plate and the roll is 0.005 inch.

In some embodiments, the camera, light source, prism, and/or plate are mounted on a device configured to reduce the variation in the distance between the plate and the roll. In some embodiments, the mounting device is a linear slide capable of manual or automatic adjustment.

In some embodiments, a sensor is used to automatically control the distance between the plate and the roll. In some embodiments, the sensor automatically maintains the distance between the plate and the roll between 0 and 0.020 inch. In some embodiments, the sensor automatically maintains the distance between the plate and the roll between 0 and 0.005 inch. In some embodiments, the sensor automatically maintains the distance between the plate and the roll at 0.005 inch.

In some embodiments, the flow rate of the coolant is controlled using a flow control valve or equivalent. In some embodiments, the flow rate of the coolant is controlled so as to remove heat generated by the grinding process while maintaining a sufficient temperature of the grinding wheel to allow for self-sharpening. In some embodiments, the flow rate of the coolant ranges from 1 gallons per minute (gpm) to 2 gpm. In some embodiments, the flow rate of the coolant ranges from 1 gpm to 3 gpm. In some embodiments, the flow rate of the coolant ranges from 1 gpm to 5 gpm. In some embodiments, the flow rate of the coolant ranges from 1 gpm to 7 gpm. In some embodiments, the flow rate of the coolant ranges from 1 gpm to 10 gpm.

In some embodiments, the method includes continuous in-process imaging of a surface of a roll. In some embodiments, the imaging is conducted during the grinding process. In some embodiments, the light source provides light for illuminating the roll. In some embodiments, the light is refracted using a prism positioned between the light source and a roll. In some embodiments, an image of the surface of the roll is received by a camera that includes at least one row of pixel sensors. In some embodiments, at least one frame produced by the camera is received by a computer system. In some embodiments, the computer system provides a two dimensional image of the roll face based, at least in part, on the at least one frame provided by the camera.

Figure 9:
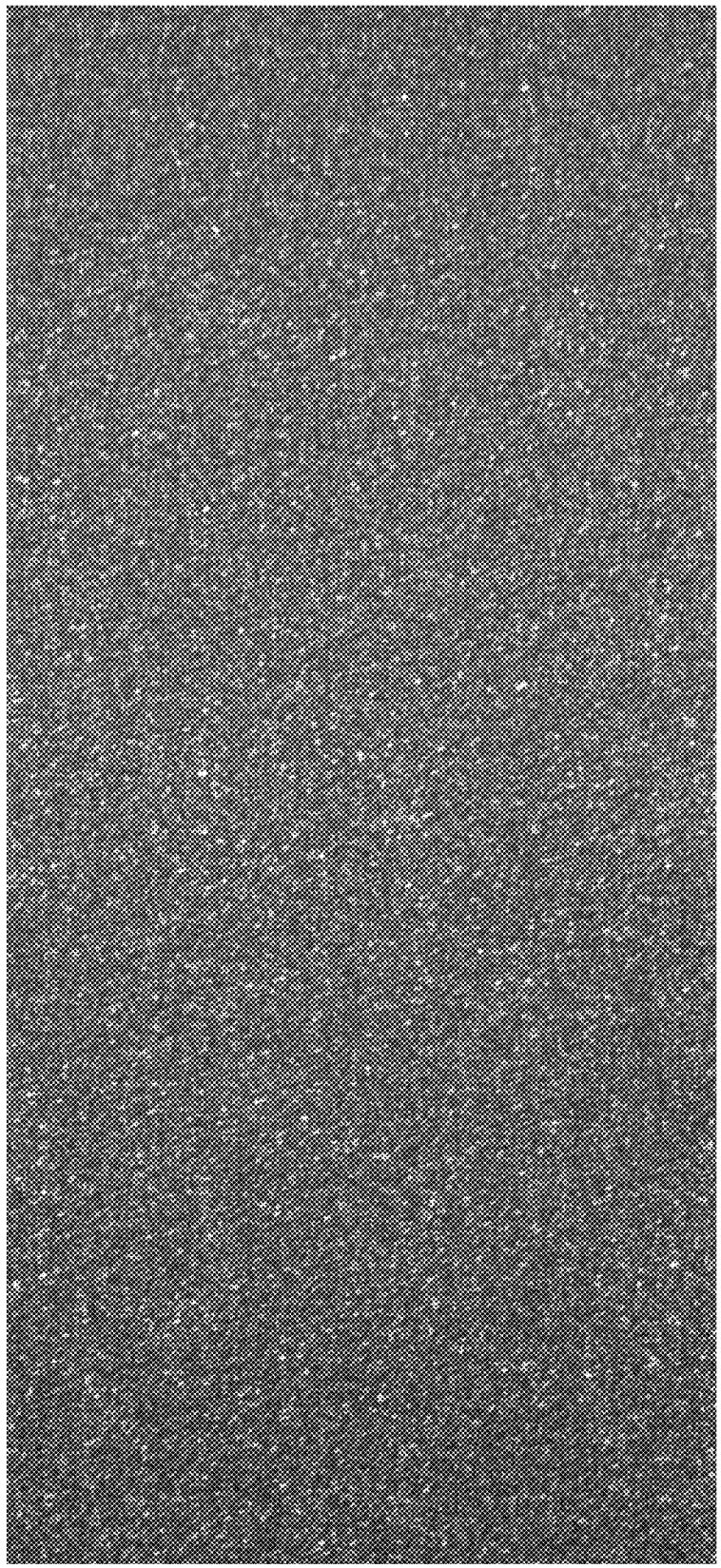
FIG. 9 illustrates a frame created by an embodiment of the method of the present invention.

A non-limiting example of a frame from the camera is shown in FIG. 9. In the non-limiting example, the frame shown in FIG. 9 is provided by a line scan camera. In the non-limiting example, the lines are provided by the camera at a speed ranging from about 1000-5000 lines per second based on the speed of the roll as the roll rotates under the view of the camera. In some embodiments the speed ranges from about 1000-10000 lines per second. In some embodiments the speed ranges from about 500-5000 lines per second. In some embodiments the speed ranges from about 100-5000 lines per second. In some embodiments the speed ranges from about 1000-4000 lines per second. In some embodiments the speed ranges from about 1000-3000 lines per second. In some embodiments the speed ranges from about 100-2000 lines per second. In some embodiments the speed ranges from about 1000-2000 lines per second. In some embodiments the speed is greater than 5000 lines per second. In some embodiments the speed is less 100 lines per second.

In some embodiments, the lines are accumulated to form a "frame". In some embodiments, the frame is formed from about 1000 lines per frame based, at least in part, on the size of the visual device used to view the frame. In some embodiments, the frames are provided at a speed ranging from about 1 to 5 frames per second. In some embodiments, the frames are provided at a speed ranging from about 1 to 10 frames per second. In some embodiments, the frames are provided at a speed ranging from about 2 to 3 frames per second. In some embodiments, the frames are provided at a speed ranging from about 1 to 7 frames per second. In some embodiments, the frames are provided at a speed ranging from about 1 to 3 frames per second. In some embodiments, the frames are provided at a speed greater than 10 frames per second. In some embodiments, the frames are provided at a speed less than 10 frames per second.

In the non-limiting example, the frame shown in FIG. 9 covers about 1 inch in the transverse direction (along the length of the roll) and about 10 inches in the circumferential direction. In the non-limiting example, lighting positioned at an angle of greater than 75 degrees causes most of the roll surface to appear dark in the frame shown in FIG. 9. In the non-limiting example, deep scratches on the surface appear as bright spots on the frame in FIG. 9.

In some embodiments, the frames may be combined together to form an image. In some embodiments, the number of frames ranges from 100 to 1000 frames. In some embodiments, the number of frames ranges from 300 to 900 frames. In some embodiments, the number of frames ranges from 600 to 800 frames. In some embodiments, the number of frames is 700 frames.

In some embodiments, the system and method combine the frames based, at least in part, on the rotational speed of the roll and the speed of the camera traversing the roll face. In some embodiments, the system and method deletes the frames and/or sections of frames that are duplicative of other frames and/or sections of frames. In some embodiments, the camera may traverse 0.1 inch of the roll for each revolution of the roll while the camera provides frames that are greater than 0.1 inch. In some embodiments, the portions of the frame that are greater than 0.1 inch are deleted during the frame combination step.

In some embodiments, the system and method use the speed of the roll and the speed of the camera traversing the roll to combine the frames into an accurate image. In some embodiments, the image may be about 5000 pixels high by about 100,000 pixels wide. In some embodiments, the image may be about 1000 pixels high by about 50,000 pixels wide. In some embodiments, the image may be about 2000 pixels high by about 100,000 pixels wide. In some embodiments, the image may be about 5000 pixels high by about 50,000 pixels wide. In some embodiments, the image may be about 10,000 pixels high by about 100,000 pixels wide. In some embodiments, the image may be about 20,000 pixels high by about 50,000 pixels wide.

In some embodiments, the system and method generate an image of the roll surface via independent control of the image resolution in the transverse and circumferential directions. In some embodiments, the resolution of the image in the transverse direction may be finer than the resolution in the circumferential direction. In some embodiments, the resolution of the image may be about 0.001 inch per pixel in the transverse direction compared with the resolution of the image in the circumferential direction of about 0.010 inch per pixel. In some embodiments, the resolution of the image may be about 0.01 inch per pixel in the transverse direction compared with the resolution of the image in the circumferential direction of about 0.1 inch per pixel. In some embodiments, the resolution of the image may be about 0.001 inch per pixel in the transverse direction compared with the resolution of the image in the circumferential direction of about 0.10 inch per pixel. In some embodiments, the resolution of the image may be about 0.1 inch per pixel in the transverse direction compared with the resolution of the image in the circumferential direction of about 0.1 inch per pixel.

In some embodiments, the system and method uses this variation in resolution in the transverse and circumferential directions to highlight defects in the roll surface.

Figure 10:
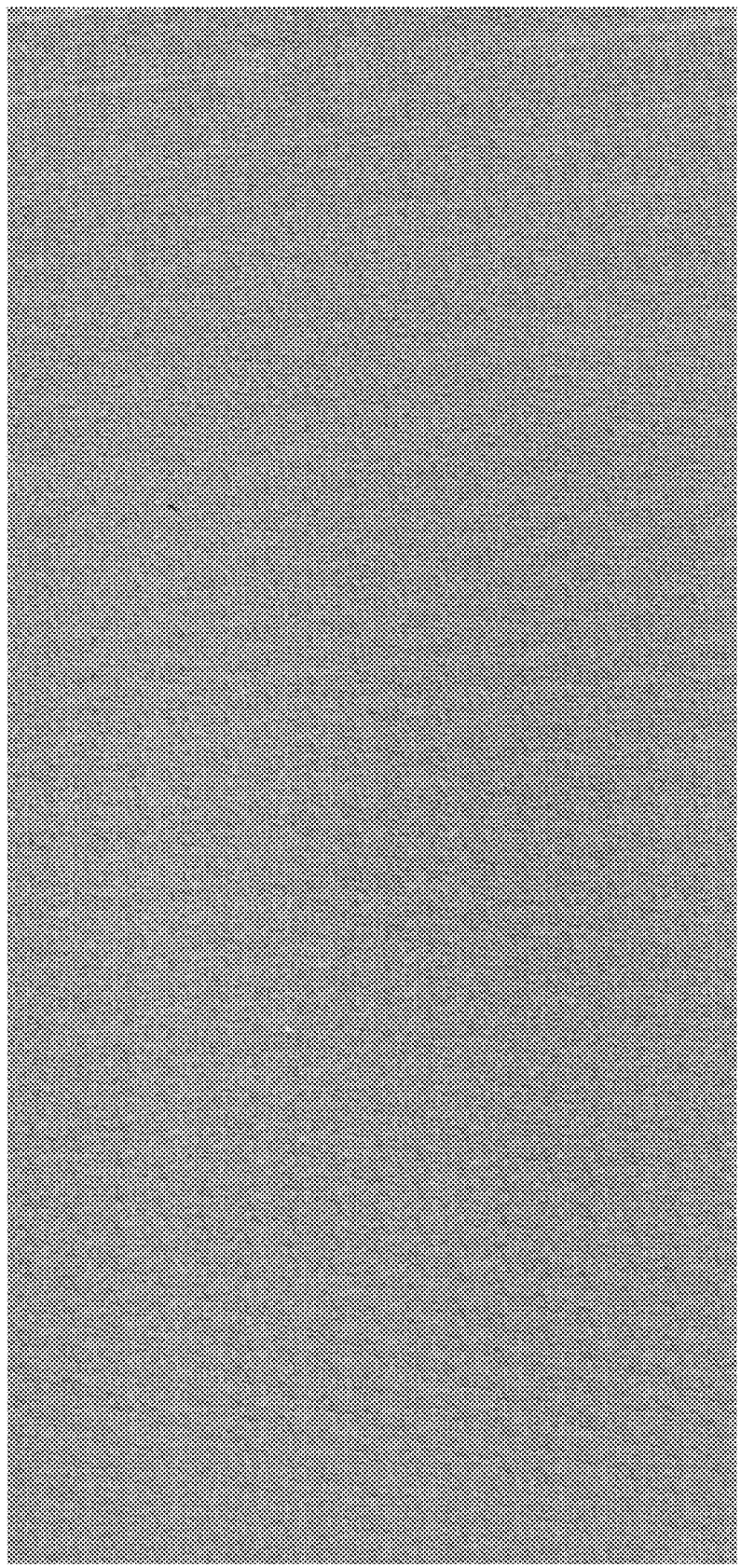
FIG. 10 illustrates an image created by an embodiment of the method of the present invention.

In a non-limiting example, the image in FIG. 10 was further modified to reduce resolution by a factor of 60 in the transverse direction and a factor of 6 in the circumferential direction to show a defect in the roll surface called a "pattern". In some embodiments, the system and method uses other modifications to the resolution in the transverse and/or circumferential directions to modify the image and/or identify other defects in a roll surface. In other embodiments, the system and method may use full resolution to identify defects in the roll surface.

A non-limiting example of a two dimensional image of a roll is shown in FIG. 10. In the non-limiting example, the image of FIG. 10 is generated using a computer system to process about 700 frames that were collected from the camera while the roll rotated and the camera traversed the roll face. In the non-limiting example, the roll surface is "unwrapped" to form a two dimensional image. In the non-limiting example, the lines and patterns on the two dimensional image indicate defects that require additional evaluation.

In some embodiments, the evaluation of the defects identified on the two dimensional image generated by the computer system is conducted manually. In some embodiments, the roll is subjected to additional grinding based at least in part on the manual evaluation of the defects identified on the two dimensional image generated by the computer system. In some embodiments, the evaluation of the defects identified on the two dimensional image generated by the computer system is conducted automatically. In some embodiments, the roll is subjected to additional grinding based at least in part on the automatic evaluation of the defects identified on the two dimensional image generated by the computer system. In some embodiments, the grinding process is continuously adjusted based, at least in part, by the automatic evaluation of the defects identified on the two dimensional image generated by the computer system.

Illustrative Operating Environments

Figure 11:
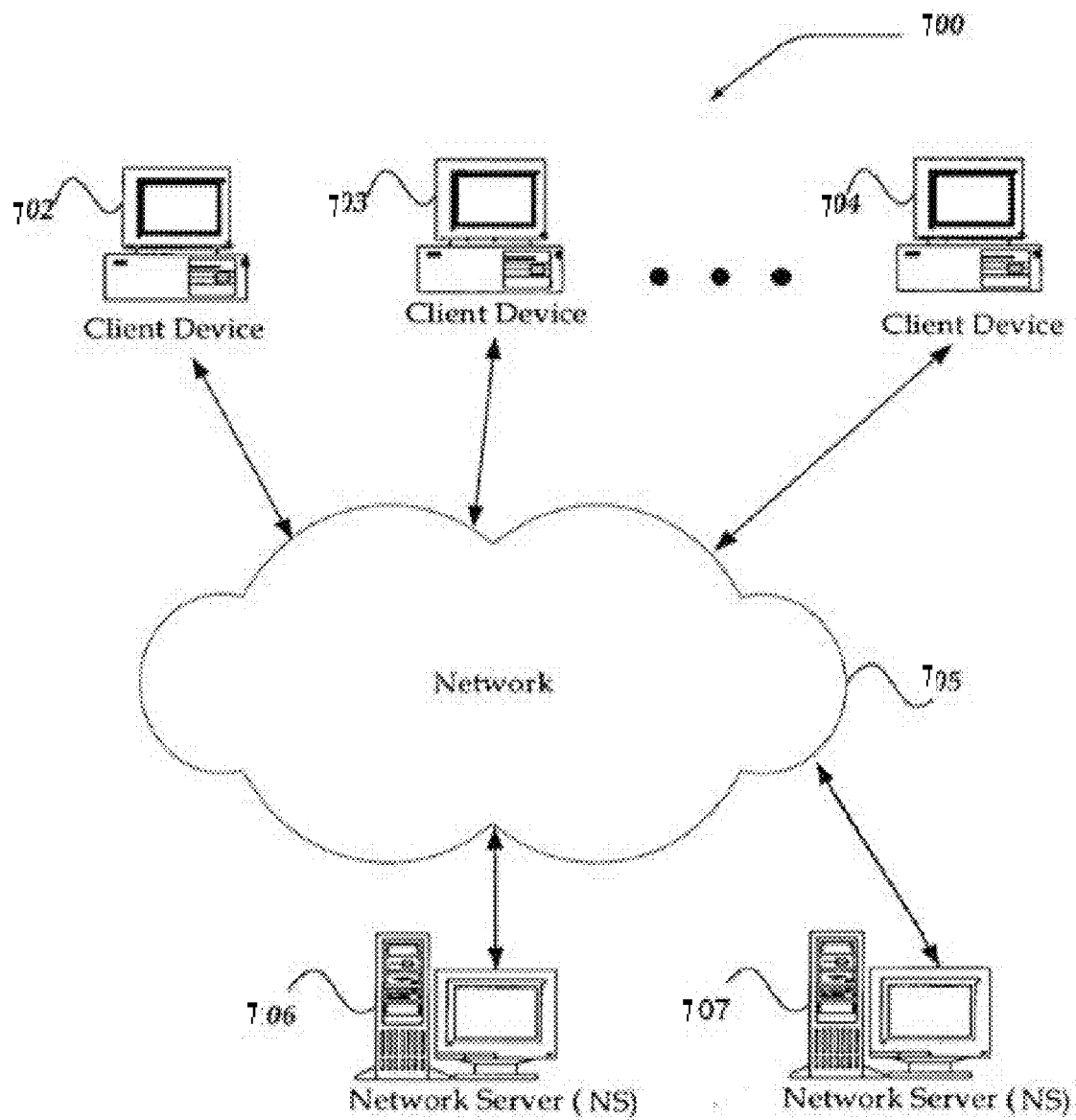
FIG. 11 illustrates features of some embodiments of the present invention.

FIG. 11 illustrates one embodiment of an environment in which the present invention may operate. However, not all of these components may be required to practice the invention, and variations in the arrangement and type of the components may be made without departing from the spirit or scope of the present invention. In some embodiments, the system and method may include a large number of members and/or concurrent transactions. In other embodiments, the system and method are based on a scalable computer and network architecture that incorporates varies strategies for assessing the data, caching, searching, and database connection pooling. An example of the scalable architecture is an architecture that is capable of operating multiple servers.

In embodiments, members of the computer system 702-704 include virtually any computing device capable of receiving and sending a message over a network, such as network 705, to and from another computing device, such as servers 706 and 707, each other, and the like. In embodiments, the set of such devices includes devices that typically connect using a wired communications medium such as personal computers, multiprocessor systems, microprocessor-based or programmable consumer electronics, network PCs, and the like. In embodiments, the set of such devices also includes devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile device, and the like. Similarly, in embodiments, client devices 702-704 are any device that is capable of connecting using a wired or wireless communication medium such as a PDA, POCKET PC, wearable computer, and any other device that is equipped to communicate over a wired and/or wireless communication medium.

In embodiments, each member device within member devices 702-704 may include a browser application that is configured to receive and to send web pages, and the like. In embodiments, the browser application may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, programming may include either Java, .Net, QT, C, C++ or other suitable programming language.

In embodiments, member devices 702-704 may be further configured to receive a message from another computing device employing another mechanism, including, but not limited to email, Short Message Service (SMS), Multimedia Message Service (MMS), instant messaging (IM), internet relay chat (IRC), mIRC, Jabber, and the like or a Proprietary protocol.

In embodiments, network 705 may be configured to couple one computing device to another computing device to enable them to communicate. In some embodiments, network 705 may be enabled to employ any form of computer readable media for communicating information from one electronic device to another. Also, in embodiments, network 705 may include a wireless interface, and/or a wired interface, such as the Internet, in addition to local area networks (LANs), wide area networks (WANs), direct connections, such as through a universal serial bus (USB) port, other forms of computer-readable media, or any combination thereof. In embodiments, on an interconnected set of LANs, including those based on differing architectures and protocols, a router may act as a link between LANs, enabling messages to be sent from one to another.

Also, in some embodiments, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. Furthermore, in some embodiments, remote computers and other related electronic devices could be remotely connected to either LANs or WANs via a modem and temporary telephone link. In essence, in some embodiments, network 705 includes any communication method by which information may travel between client devices 702-704, and servers 706 and 707.

Figure 12:
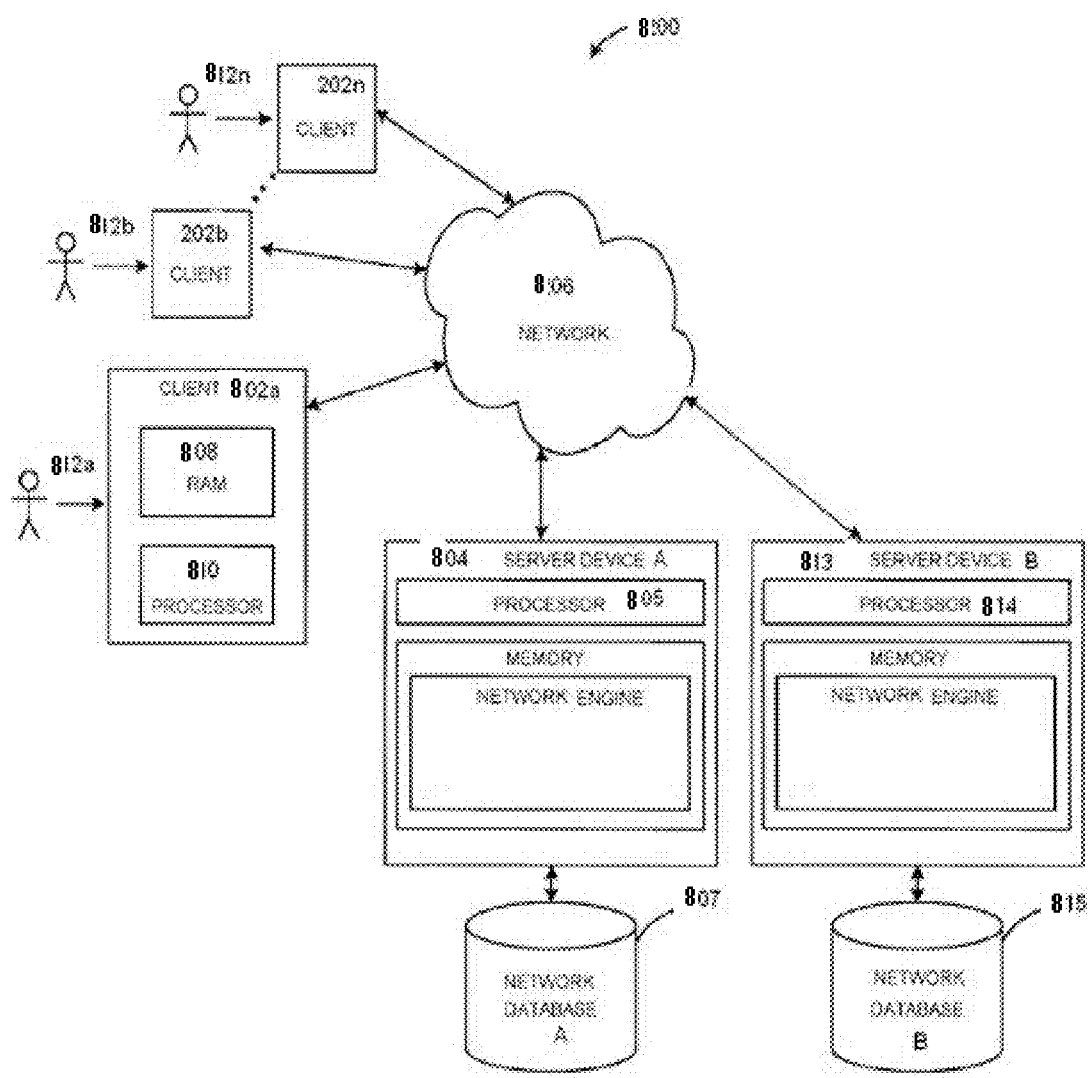
FIG. 12 illustrates features of some embodiments of the present invention.

FIG. 12 shows another exemplary embodiment of the computer and network architecture that supports the method and system. The member devices 802*a*, 802*b* thru 802*n* shown each at least includes a computer-readable medium, such as a random access memory (RAM) 808 coupled to a processor 810 or FLASH memory. The processor 810 may execute computer-executable program instructions stored in memory 808. Such processors comprise a microprocessor, an ASIC, and state machines. Such processors comprise, or may be in communication with, media, for example computer-readable media, which stores instructions that, when executed by the processor, cause the processor to perform the steps described herein. Embodiments of computer-readable media may include, but are not limited to, an electronic, optical, magnetic, or other storage or transmission device capable of providing a processor, such as the processor 810 of client 802*a*, with computer-readable instructions. Other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript Member devices 802*a-n* may also comprise a number of external or internal devices such as a mouse, a CD-ROM, DVD, a keyboard, a display, or other input or output devices. Examples of client devices 802*a-n* may be personal computers, digital assistants, personal digital assistants, cellular phones, mobile phones, smart phones, pagers, digital tablets, laptop computers, Internet appliances, and other processor-based devices. In general, a client device 802*a* are any type of processor-based platform that is connected to a network 806 and that interacts with one or more application programs. Client devices 802*a-n* may operate on any operating system capable of supporting a browser or browser-enabled application, such as Microsoft™, Windows™, or Linux. The client devices 802*a-n* shown may include, for example, personal computers executing a browser application program such as Microsoft Corporation's Internet Explorer™, Apple Computer, Inc.'s Safari™, Mozilla Firefox, and Opera. Through the client devices 802*a-n*, users, 812*a-n* communicate over the network 806 with each other and with other systems and devices coupled to the network 806. As shown in FIG. 12, server devices 804 and 813 may be also coupled to the network 806.

In some embodiments, the term "mobile electronic device" may refer to any portable electronic device that may or may not be enabled with location tracking functionality. For example, a mobile electronic device can include, but is not limited to, a mobile phone, Personal Digital Assistant (PDA), Blackberry™, Pager, Smartphone, or any other reasonable mobile electronic device. For ease, at times the above variations are not listed or are only partially listed, this is in no way meant to be a limitation.

In some embodiments, the terms "proximity detection," "locating," "location data," "location information," and "location tracking" as used herein may refer to any form of location tracking technology or locating method that can be used to provide a location of a mobile electronic device, such as, but not limited to, at least one of location information manually input by a user, such as, but not limited to entering the city, town, municipality, zip code, area code, cross streets, or by any other reasonable entry to determine a geographical area; Global Positions Systems (GPS); GPS accessed using Bluetooth™; GPS accessed using any reasonable form of wireless and/or non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed, this is in no way meant to be a limitation.

In some embodiments, near-field wireless communication (NFC) can represent a short-range wireless communications technology in which NFC-enabled devices are "swiped," "bumped," "tap" or otherwise moved in close proximity to communicate. In some embodiments, NFC could include a set of short-range wireless technologies, typically requiring a distance of 10 cm or less.

In some embodiments, NFC may operate at 13.56 MHz on ISO/IEC 18000-3 air interface and at rates ranging from 106 kbit/s to 424 kbit/s. In some embodiments, NFC can involve an initiator and a target; the initiator actively generates an RF field that can power a passive target. In some embodiment, this can enable NFC targets to take very simple form factors such as tags, stickers, key fobs, or cards that do not require batteries. In some embodiments, NFC peer-to-peer communication can be conducted when a plurality of NFC-enable devices within close proximity of each other.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated)

We claim:
1. A system comprising:
(i) a prism,
(ii) a camera,
(iii) a light source, and
(iv) a plate;
wherein the system is configured for scanning a roll and generating an image of a surface of the roll;
wherein the prism is positioned below the camera and above the plate;
wherein the plate is positioned below the prism and on or above the surface of the roll;
wherein the light source is positioned above the prism;
wherein the light source and the prism are positioned to provide light to the surface of the roll at an angle of at least 75 degrees as measured from a line normal to the surface of the roll;
wherein the prism is configured to refract light from the light source;
wherein the camera is a line scan camera that includes at least one row of pixel sensors; and
wherein the light source includes one or more light emitting diodes.

2. The system of claim 1, wherein the plate is positioned between 0.005 inches and 0.05 inches from the roll.

3. The system of claim 2, wherein the plate is positioned between 0.005 and 0.020 inches from the roll.

4. The system of claim 3, wherein the plate is positioned 0.005 inches from the roll.

5. The system of claim 1, wherein a coolant is positioned between the plate and the roll.

6. The system of claim 1, wherein the plate comprises a polymeric material.

7. The system of claim 1, wherein the light source and the prism are positioned to provide light at an angle of 78 degrees as measured from the line normal to the surface of the roll.

* * * * *